(12) United States Patent
Sutermeister et al.

(10) Patent No.: US 11,147,874 B2
(45) Date of Patent: Oct. 19, 2021

(54) DEVICES AND METHODS FOR THERAPEUTIC HEAT TREATMENT

(71) Applicant: Boston Scientific Scimed, Inc., Maple Grove, MN (US)

(72) Inventors: Derek C. Sutermeister, Ham Lake, MN (US); Martin R. Willard, Burnsville, MN (US); Patrick A. Haverkost, Brooklyn Center, MN (US); Timothy A. Ostroot, Cokato, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 466 days.

(21) Appl. No.: 15/183,013

(22) Filed: Jun. 15, 2016

(65) Prior Publication Data

US 2016/0361417 A1    Dec. 15, 2016

Related U.S. Application Data

(60) Provisional application No. 62/175,837, filed on Jun. 15, 2015.

(51) Int. Cl.
*A61K 41/00* (2020.01)
*A61N 1/40* (2006.01)
(Continued)

(52) U.S. Cl.
CPC .......... *A61K 41/0052* (2013.01); *A61N 2/004* (2013.01); *A61K 9/0009* (2013.01);
(Continued)

(58) Field of Classification Search
CPC .......... A61B 18/04; A61B 2018/00125; A61B 2018/00136; A61B 2018/00148;
(Continued)

(56) References Cited

U.S. PATENT DOCUMENTS 6,120,856 A * 9/2000 Liberti ................ A61K 9/5094
252/62.56
2003/0180370 A1    9/2003 Lesniak et al.
(Continued)

FOREIGN PATENT DOCUMENTS

CN    101284161    10/2008
JP    H06245993    9/1994
(Continued)

OTHER PUBLICATIONS

Martinez-Boubeta, C. et al (2012), Adjustable Hyperthermia Response of Self-Assembled Ferromagnetic Fe—MgO Core-Shell Nanoparticles by Tuning Dipole-Dipole Interactions. Adv. Funct. Mater., 22: 3737-3744. (Year: 2012).*
(Continued)

*Primary Examiner* — Kaitlyn E Smith
*Assistant Examiner* — Rachel A. Vierra
(74) *Attorney, Agent, or Firm* — Pauly, DeVries Smith & Deffner LLC

(57) ABSTRACT

An example implantable microparticle for delivering therapeutic heat treatment comprises a generally spherical body. The body may be formed from a first material comprising a biodegradable material and a second material comprising a Curie temperature material. The biodegradable material may be a non-Curie temperature material or have a Curie temperature lower than a Curie temperature of the Curie temperature material. The first material and the second material are mixed to form a composite having a Curie temperature in the range of 35° C. and 100° C.

18 Claims, 2 Drawing Sheets

(51) Int. Cl.
*A61N 2/00* (2006.01)
*A61K 9/50* (2006.01)
*A61K 9/00* (2006.01)

(52) U.S. Cl.
CPC ............ *A61K 9/501* (2013.01); *A61K 9/5094* (2013.01); *A61N 1/406* (2013.01)

(58) Field of Classification Search
CPC ...... A61B 2018/00154; A61K 41/0052; A61K 9/0009; A61K 9/501; A61K 9/5094; A61N 1/406; A61N 2/004
See application file for complete search history.

(56) References Cited

U.S. PATENT DOCUMENTS

| | | | | |
|---|---|---|---|---|
| 2004/0101564 | A1* | 5/2004 | Rioux | A61K 9/0009 424/488 |
| 2005/0021088 | A1* | 1/2005 | Schuler | A61B 18/04 607/1 |
| 2006/0018948 | A1 | 1/2006 | Guire et al. | |
| 2009/0157069 | A1 | 6/2009 | Tom et al. | |
| 2010/0099941 | A1* | 4/2010 | Haik | A61K 33/24 600/12 |
| 2010/0163777 | A1 | 7/2010 | Nakahama | |
| 2013/0243699 | A1* | 9/2013 | Wang | B22F 1/0018 424/9.32 |
| 2014/0249351 | A1* | 9/2014 | Jones | A61N 1/406 600/10 |
| 2015/0297281 | A1 | 10/2015 | Sutermeister et al. | |
| 2015/0297763 | A1* | 10/2015 | Sutermeister | A61K 47/6957 424/1.61 |

FOREIGN PATENT DOCUMENTS

| | | |
|---|---|---|
| JP | 2006206416 | 8/2006 |
| JP | 2011506317 | 6/2009 |
| JP | 2011032238 | 2/2011 |
| JP | 2015528052 | 9/2015 |
| WO | 2003037202 | 5/2003 |
| WO | 2004020011 | 3/2004 |
| WO | 2007116954 | 10/2007 |
| WO | 2014001191 | 1/2014 |

OTHER PUBLICATIONS

Sharma, G. et al, Single step thermal decomposition approach to prepare supported γ-Fe2O3 nanoparticles. Applied Surface Science (2012), 3679-3688. (Year: 2012).*
"Office Action," for Japanese Patent Application No. 2017-550896 dated Jul. 17, 2018 (8 pages) with English translation.
"Communication Pursuant to Rules 161(1) and 162 EPC," for European Patent Application No. 16735961.1 dated Oct. 5, 2017 (2 pages).
"International Search Report and Written Opinion," for PCT Application No. PCT/US2016/037518 dated Sep. 15, 2016 (12 pages).
"Response to Communication Pursuant to Rules 161(1) and 162 EPC," for European Patent Application No. 16735961.1 filed with the EPO Mar. 21, 2018 (22 pages).
"Final Office Action," for Japanese Patent Application No. 2017-550896 dated Dec. 11, 2018 (6 pages) with English Translation.
Wang, Qian et al., "Biodegradable magnesium nanoparticle-enhanced laser hyperthermia therapy," International Journal of Nanomedicine 2012, vol. 7, pp. 4715-4725 (11 pages).
"First Office Action," for Chinese Patent Application No. 201680033953.5 dated Jan. 22, 2020 (13 pages) with English Summary.
"Second Office Action," for Chinese Patent Application No. 201680033953.5 dated Sep. 25, 2020 (6 pages) with English Summary.
"Communication Pursuant to Article 94(3) EPC," for European Patent Application No. 16735961.1 dated May 3, 2021 (8 pages).
"Decision of Rejection," for Chinese Patent Application No. 201680033953.5 dated Mar. 17, 2021 (9 pages) with English Summary.
"Response to Communication Pursuant to Article 94(3) EPC," for European Patent Application No. 16735961.1 filed Jul. 12, 2021 (27 pages).

* cited by examiner

DEVICES AND METHODS FOR THERAPEUTIC HEAT TREATMENT

CROSS-REFERENCE TO RELATED APPLICATIONS

This application claims the benefit of priority under 35 U.S.C. § 119 to U.S. Provisional Patent Application No. 62/175,837 titled "DEVICES AND METHODS FOR THERAPEUTIC HEAT TREATMENT" by Sutermeister, et al. and filed Jun. 15, 2015, which is incorporated by reference in its entirety and for all purposes.

BACKGROUND

Delivering heat (e.g., to biological tissue, etc.) can be used in and/or in conjunction with various treatments and procedures (e.g., medical procedures, etc.). For example, some medical devices (e.g., catheters, etc.) have been used to ablate diseased or undesired biological tissue (e.g., nerves) or to deliver heat for treating diseases (e.g., cancer, etc.). Medical devices have included complex control equipment (e.g., thermal sensors coupled with additional control systems) to deliver controlled (e.g., isothermal) thermal energy to a target site. In some instances, controlling temperature (e.g., spatial homogeneous distribution, maximum heating temperature, etc.) is useful to deliver heat to a target site, while reducing and/or avoiding heat delivery and/or damage to surrounding tissue. For regulating temperature of the devices, an independent control (e.g., energy control, temperature control, etc.) and a number of power and ground wires have been used. Therefore, there is a need to develop new ways for delivering heat (e.g., with temperature control).

Heat delivery devices have used Curie temperature materials. When subjected to a field of sufficient intensity, a Curie temperature material heats up to a characteristic temperature at which its magnetic properties switch to paramagnetic properties and at which the temperature of the Curie temperature material stops increasing. One problem that has been encountered in the use of Curie temperature materials for heat delivery is the problem of inefficient coupling of the heat generated (by the temperature increase of the Curie temperature material due to the applied field) to the surrounding environment (e.g., a target for heat delivery). For example, a composition containing a low weight percentage of Curie temperature material may exhibit uneven temperatures or uneven thermal conductivity across a heat delivery device due to the presence of other components in the composition. Therefore, there is a need for improved heat delivery compositions.

SUMMARY

This disclosure provides design, material, manufacturing method, and use alternatives for medical devices.

An example medical device comprises an implantable microparticle including a generally spherical body, the body including a first material comprising a biodegradable material; a second material comprising a Curie temperature material; wherein the biodegradable material is a non-Curie temperature material or has a Curie temperature lower than a Curie temperature of the Curie temperature material; and wherein the first material and the second material are mixed to form a composite having a Curie temperature in the range of 35° C. and 100° C.

Alternatively or additionally to any of the embodiments above, a ratio of first material to the second material is greater than 1:1.

Alternatively or additionally to any of the embodiments above, the first material comprises a magnesium based compound.

Alternatively or additionally to any of the embodiments above, the first material comprises magnesium oxide.

Alternatively or additionally to any of the embodiments above, the first material comprises a biocompatible polymer Alternatively or additionally to any of the embodiments above, the second material comprises an iron oxide.

Alternatively or additionally to any of the embodiments above, the second material comprises an iron alloy.

Alternatively or additionally to any of the embodiments above, the second material comprises a plurality of nanoparticles.

Alternatively or additionally to any of the embodiments above, the plurality of nanoparticles each have a particle size in the range of 0.1 to 2.5 nanometers.

Alternatively or additionally to any of the embodiments above, further comprising a therapeutic agent.

Alternatively or additionally to any of the embodiments above, the therapeutic agent is disposed on an outer surface of the spherical body.

Alternatively or additionally to any of the embodiments above, the therapeutic is intermixed with the first material and the second material.

Alternatively or additionally to any of the embodiments above, the microparticle is configured to degrade over a period of time.

Alternatively or additionally to any of the embodiments above, the period of time is in the range of 3 to 6 months.

Alternatively or additionally to any of the embodiments above, the microparticle has a diameter in the range of 1-3000 microns.

Another example implantable microparticle includes a first material comprising magnesium oxide; and a second material comprising an iron oxide; wherein the first material and the second material are mixed in a ratio of greater than 1:1 to form an alloy having a Curie temperature in the range of 35° C. and 100° C.

An example method of delivering therapeutic heat to a location within the body includes implanting at least one microparticle into a body adjacent to a desired treatment region, the microparticle including a generally spherical body, the body comprising: a first material comprising a biodegradable material; a second material comprising a Curie temperature material; wherein the biodegradable material is a non-Curie temperature material or has a Curie temperature lower than a Curie temperature of the Curie temperature material; and wherein the first material and the second material are mixed to form an alloy having a Curie temperature in the range of 35° C. and 100° C. generating a magnetic field at a location adjacent to the microparticle for a period of time to heat the microparticle to its Curie temperature; and maintaining the microparticle at its Curie temperature for a treatment of time to achieve the desired therapeutic effect.

Alternatively or additionally to any of the embodiments above, the steps of generating a magnetic field and maintaining the microparticle at its Curie temperature are repeated in discrete sessions separated by a length of time.

Alternatively or additionally to any of the embodiments above, the steps of generating a magnetic field and maintaining the microparticle at its Curie temperature are repeated without implanting any additional microparticles.

Alternatively or additionally to any of the embodiments above, the microparticle further comprise a therapeutic agent.

Alternatively or additionally to any of the embodiments above, the microparticle has a diameter in the range of 1-3000 microns.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
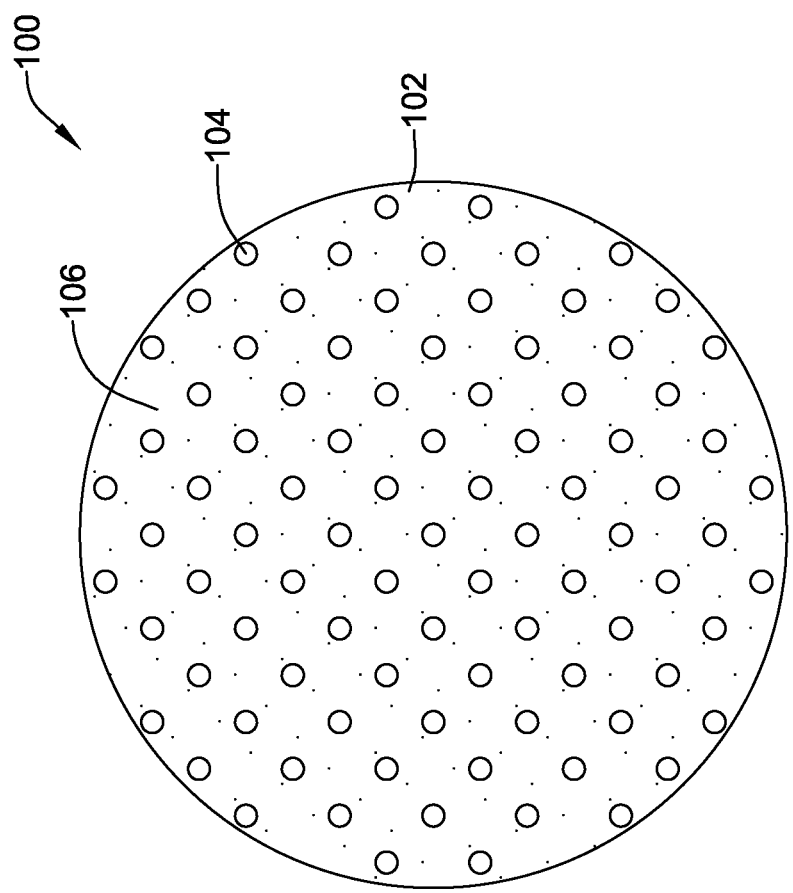
FIG. 1 is cross-sectional view of an illustrative microparticle.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure.

DETAILED DESCRIPTION

For the following defined terms, these definitions shall be applied, unless a different definition is given in the claims or elsewhere in this specification.

As used herein, "Curie temperature" or "Tc" refers to a critical temperature below which a material (e.g., a ferromagnet, etc.) exhibits magnetic properties and at or above which the material exhibits paramagnetic properties.

As used herein, "Curie material" or "Curie temperature material" refers to a ferromagnetic, ferrimagnetic, or antiferromagnetic material that exhibits paramagnetic properties above the material's Curie temperature.

Curie temperature of a Curie material may be altered by using composite materials, which may or may not be ferromagnetic. Changes in doping, additives, composites, alloying, and density of Curie materials can alter their structure and behavior to alter the Curie temperature.

"Non-Curie material" or "non-Curie temperature material" refers to an organic or inorganic material (e.g., non-magnetic material, etc.) such as a metal, a metal oxide, a metal salt, a non-metal, a polymer, and combinations thereof that do not have a Curie temperature.

A "homogenous mixture" refers to a type of mixture in which the composition is uniform and every part of the solution has the same properties. In the present disclosure, a homogeneous mixture of a metallic Curie temperature material with a metallic secondary material may also be referred to as an alloy. In the present disclosure, a "secondary material" refers to an inorganic material (i.e., one that does not include carbon such as a polymer, etc.).

The term "metal" refers to an electropositive chemical element. The term "non-metal" refers to a chemical element that does not have the capacity to lose electrons and form a positive ion. For the purpose of this disclosure, metalloids (e.g., Si) are considered to be non-metals.

As used herein, a "thermoset" polymer (e.g., a thermoset) refers to a polymer that, once having been cured (or hardened) by a chemical reaction (e.g., covalent bond forming, crosslinking, etc.), will not soften or melt when subsequently heated.

As used herein, a "thermoplastic" polymer (e.g., a thermoplast) refers to a polymeric material that softens when heated and hardens upon cooling, processes that are reversible and repeatable.

As used herein, "particle size" of a particle refers to the largest dimension (chosen from length, width, and height) of the particle. For example, for a spherical particle, the largest dimension is the diameter. As used herein, the "particle size" of a plurality of particles refers to the average (i.e., mean) of the particle sizes of the particles, based on the population of particles. As used herein, a "range of particle size" of a plurality of particles refers to a range in which at least ninety percent of the population of particles has a particle size within that range, allowing for a combined up to ten percent of the population of particles to be above the recited range and below the recited range. For example, a range of particle size of a plurality of particles of from 1 nanometer to 100 nanometers refers to a plurality of particles wherein at least ninety percent of the population of particles has a particle size from 1 nanometer to 100 nanometers (meaning that the sum of the populations of particles less than 1 nanometer and particles greater than 100 nanometers does not exceed 10% of the total population), with 0-10% of the population being less than 1 nanometer and 0-10% of the population being greater than 100 nanometers.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Hyperthermia provides localized thermal treatment of tumor cells and lacks any cumulative toxicity in contrast to chemotherapy and radiotherapy. A variety of hyperthermia therapeutic approaches are used for treatment of tumors. One such approach involves deployment of magnetic nanoparticles to a tumor site. These magnetic nanoparticles have a selected Curie temperature and generate heat when subjected to an applied alternating field. One problem that has been encountered in the use of Curie temperature materials for heat delivery is the problem of inefficient coupling of the heat generated (by the temperature increase of the Curie temperature material due to the applied field) to the surrounding environment (e.g., a target for heat delivery). For example, a composition containing a low weight percentage of Curie temperature material may exhibit uneven temperatures or uneven thermal conductivity across a heat delivery device due to the presence of other components in the composition. Therefore, there is a need for improved heat delivery compositions. While the present disclosure is discussed relative to the thermal treatment of tumor cells, it is contemplated that the devices and methods described herein can be applied to other parts of the anatomy where hyperthermia treatments or the controlled application of heat is desired. For example, the devices and methods may be applied to other parts of the anatomy, such as, but not limited to, the vasculature, the nervous system, gastrointestinal, urological, gynecological, etc.

While large particles provide location stability when deployed to a tumor site for hyperthermia treatment, the large size may prevent the particles from being expelled from the body. Typical magnetic materials do not degrade within the body to allow for expulsion from the body. It may be desirable to provide a particle that may efficiently and/or uniformly heat a tumor, or other target region, and the surrounding tissue to a predetermined temperature, remain in the body for a predetermined amount of time, and then be naturally resorbed or expelled from the body.

Magnesium based alloys may degrade due to corrosion when placed in an aqueous solution or substance. This may allow magnesium based alloys to degrade when placed within the body due to high oxidative corrosion rates of magnesium. While magnesium may make a suitable temporary implant, it may not be suitable for hyperthermia treatments using magnetic fields as a means for heating the implant and thus the surrounding tissue. For example, magnesium based compounds or alloys may have a Curie temperature well below body temperature or room temperature. In one example, magnesium oxide (MgO) has a Curie temperature in the range of 15 Kelvin (K) (−258 degrees Celsius (° C.)). This is just one example. Combining a magnesium based compound or alloy, for example one having a Curie temperature in the range of 310 to 318 K (37 to 45° C.) or less, with a material having a relatively high Curie temperature (e.g. 700 to 950 K or 427 to 677° C.) may generate an alloy or composition with a Curie temperature in the range of 38° C. degrees Celsius to about 45° C. or in a range of about 55° C. to about 95° C.

In addition, combining magnesium based compounds or alloy with a second material can yield a magnesium based alloy that is large enough in size, for location stability but will also breakdown and be naturally resorbed or expelled by the body while still having magnetic properties that allow the composition to be heated. Such magnesium based alloy sizes can be, for example, greater than or equal to 20 microns (μm). In addition, particle size and/or distribution may have an effect on the ability to achieve a consistent specific absorption rate (SAR) and effective heating properties.

In one or more embodiments, the composition includes a mixture that includes a first Curie temperature material and a second Curie temperature material that is different from the first Curie temperature material. In some embodiments, a third Curie temperature material may be included in the composition with the first and second Curie temperature materials. In other embodiments, a Curie temperature material may be mixed with a non-Curie temperature material. Suitable materials for each of the first, second, and third Curie temperature materials include any Curie temperature material including, but not limited to, the Curie temperature materials disclosed herein. In one or more embodiments, a mixture of one or more Curie temperature materials exhibits a Curie temperature in a range of about 38° C. to about 45° C. or in a range of about 55° C. to about 95° C. In some embodiments, a mixture of first and second Curie temperature materials includes an alloy of the first and second Curie temperature materials. In some embodiments, a mixture of first and second Curie temperature materials includes a first Curie temperature material doped with a second Curie temperature material. In one or more embodiments, a mixture of first and second Curie temperature materials includes a nanocomposite (e.g., a composite of two materials in the form of a nanoparticle, etc.) of the first and second Curie temperature materials.

In one or more embodiments, the Curie temperature material includes one or more of gallium, lanthanum, iron, cobalt, or nickel, or compounds thereof. In one or more embodiments, the Curie temperature material includes one or more of gallium arsenide, dysprosium, lanthanum iron oxide, lanthanide (e.g. LaFe—Si—H) particles, cobalt, magnetite, and neodymium. Numerous additional Curie temperature materials useful for the practice of embodiments of the present disclosure may be selected from those described in commonly assigned U.S. patent application Ser. No. 14/689,605, the entire disclosure of which is hereby incorporated by reference.

In one or more applications of heat delivery (e.g., therapeutic heat delivery), a particular Curie temperature or a range of Curie temperatures may be desired. In the present disclosure, it is contemplated that a composition may be selected with a target Curie temperature (or range of Curie temperatures) to provide a desired temperature treatment to a subject (e.g., the object to be heat treated, tissue to be heat treated, etc.). It should be recognized that one of skill in the art may select a Curie temperature material having a Curie temperature and may tune that Curie temperature by, for example, modifying chemical composition (e.g., mixing, doping, etc.), modifying shape (e.g., providing spherical particles, providing non-spherical particles), modifying particle size, and/or modifying domain control of the composition to reach a desired temperature of heat delivery.

For example, particle size in a crystal lattice changes Curie temperature. Although not wishing to be bound by theory, as particle size decreases, the fluctuations in electron spins can become more significant, causing disorder in magnetic moments and lowering Curie temperature. For example, in superparamagnetism, magnetic moments change randomly, creating disorder in small ferromagnetic particles. In some instances, by reducing the particle size to the nanometer scale, the specific absorption rate, or magnetic absorbance, may be increased by a factor of around 10. The specific absorption rate may be dependent on the concentration of the magnetic particles. The higher the concentration, the greater the specific absorption rate may be.

FIG. 1 is a cross-sectional view of an embodiment of an implantable therapeutic device 100. In some embodiments, the implantable therapeutic device 100 comprises a microparticle. The microparticle 100 may have a generally spherical shape, although this is not required. It is contemplated that the therapeutic device 100 may take any shape desired. For example, the microparticles 100 may be rod-shaped, elliptical, or an eccentric shape. In some instances, nanoparticles may be used for cellular uptake. In some embodiments, the implantable therapeutic device 100 may have a generally spherical body formed from a composition having a first material 102 and a second material 104. While the second material 104 is illustrated as discrete particles, this is for illustrative purposes only. The second material 104 may be homogenously or heterogeneously mixed with the first material 102 to form a solid solution, composite and/or alloy. The first material 102 may comprise a biodegradable, low temperature Curie temperature material, a non-Curie temperature material, or other Curie temperature material, as desired. The second material 104 may comprise a Curie temperature material and, in some instances, may be magnetic nanoparticles that are made of Curie materials. The term "magnetic nanoparticles" includes anti-ferromagnetic, ferromagnetic, ferrimagnetic, and/or magnetocaloric materials. In some embodiments, the first material 102 and/or the second material 104 is formed from one or more materials such that the implantable device 100 has a selected Curie temperature ($T_c$) between 35° C. and 100° C. In some embodiments, the implantable device 100 has a Curie temperature of approximately 80° C. When the implantable device 100 is subjected to an alternating magnetic field, the second material 104 undergoes power dissipation in the form of heat caused by relaxation phenomena of the particles' magnetic moments following the electromagnetic field and the mechanical rotation of particles themselves within the dispersant medium. At temperatures less than the Curie temperature ($T<T_c$), the second material 104 is ferro- (or ferri-) magnetic, whereas the second material 104 transitions into a paramagnetic phase to stabilize the second material 104 temperature at the predetermined Curie temperature.

In some embodiments, the first material 102 may be a magnesium alloy or compound, such as, but not limited to MgO. Because magnesium degrades in the body over time, combining magnesium with a Curie temperature material may produce a microparticle 100 large enough for particle stability while providing particle breakdown and removal after therapy. The implantable microparticle 100 can range in size from 1 micron (μm) to 3,000 microns, based on the intended purpose for treatment of the tissue. The implantable therapeutic device 100 can also be smaller than 1 micron and larger than 30,000 microns, as desired. In some embodiments, the particle 100 may be in the range of 1 nanometer (nm) to 1,000 nm. For example, the implantable therapeutic device 100 may be sized according to the location in which it is to be implanted.

In some embodiments, the implantable therapeutic device 100 may be injected, or otherwise implanted, into the body to occlude the vascular bed of the undesirable tissue due to its predetermined size in the given size range. Such implantable therapeutic devices 100 may function to block the oxygen supply, in addition to delivering heat and/or a therapeutic drug, to the tissue for treatment. In other embodiments, the implantable therapeutic device 100 may be injected, or otherwise implanted, into the body or bulk of the tumor or undesirable tissue.

Combining MgO with an iron, iron oxide, or an iron alloy may achieve an alloy having a Curie temperature substantially reduced from similar sized particles made of only iron oxide. It is contemplated that the alloy may be made through known processes, including but not limited to, arc melting, melt spinning, etc. Some example iron oxides to include, but are not limited to, iron (III) oxide ($Fe_2O_3$) having a Curie temperature of approximately 675° C. (948 K), iron (II, III) oxide ($FeO.Fe_2O_3$) having a Curie temperature of approximately 585° C. (858 K), and magnesium oxide iron (III) oxide ($MgOFe_2O_3$) having a Curie temperature of approximately 440° C. (713 K). While the microparticle 100 is described with respect to a magnesium oxide/iron blend, it should be understood that other low Curie temperature materials or non-Curie temperature materials may be used in place of or in addition to the MgO and other Curie temperature materials may be used in place of or in addition to the iron.

In some embodiments, the microparticle 100 may be formed by compounding or alloying the first material 102 (such as MgO) with the second material 104 (such as iron (III) oxide) in a ratio of greater than 1:1 such that the microparticle includes more of the first material 102 (e.g. the relatively low Curie temperature material or non-Curie temperature materials) than the second material 104 (the relatively high Curie temperature material). However, this is just an example. It is contemplated that the ratio of the first material 102 to the second material 104, the types of materials 102, 104, and/or size of the particles may be selected to achieve an appropriate Curie temperature, a desired magnetic susceptibility, biocompatibility, location stability, and/or particle elimination (post therapy). In some embodiments, the percentage of the Curie temperature material 104 in the composition or microparticle 100 (e.g., by weight percent) may depend on a variety of factors, for example: (1) the type of treatment, (2) the amount of heat required for treatment, (3) the type of body tissue, etc. In some embodiments, the Curie temperature material 104 comprise at least 2% of the device 100 by weight. In some embodiments, however, the Curie temperature material 104 comprise at least 3% of the device 100 by weight. Other suitable percentages of the Curie temperature material 104 in the device 100 may include at least 4%, 5%, 8%, 15%, etc., by weight. It should be noted that any other suitable percentage of the Curie temperature material 104 may also be contemplated, without departing from the scope of the present disclosure.

Once implanted into a body, adjacent to a desired treatment region, the therapeutic device 100 may be subjected to an alternating electric or magnetic field. The electric or magnetic field may be applied or generated from a location external to the body and directed at the location of the therapeutic device(s) 100. When subjected to a field of sufficient intensity, the therapeutic device 100 heats up to a characteristic temperature at which the magnetic properties of the Curie temperature material 104 switch to paramagnetic properties and at which the temperature of the Curie temperature material stops increasing. The device 100 heats only in the presence of a specified electric or magnetic field and frequency and only to the Curie temperature of the Curie temperature material 104. When the Curie temperature is reached, the material goes from magnetic to non-magnetic, discontinuing the heating. This is a cyclic process that permanently and rapidly maintains the therapeutic device 100 temperature at the set Curie point of the material, as long as the electric or magnetic field is applied. The electric or magnetic field may be applied for any length of time to achieve the desired hyperthermic treatment. It contemplated that the hyperthermic treatment may be performed over a period of seconds or minutes. In some instances, the hyperthermic treatment may be performed over a duration in the range of 15 to 120 minutes or in the range of 30 to 90 minutes.

It is contemplated that the therapeutic device 100 may be configured to remain the in body for a desired period of time. For example, the therapeutic device 100 may be used to deliver hyperthermic treatments in combination with chemotherapy or radiation in the treatment of cancer. These treatments may be delivered in discrete sessions over a period of weeks or months without the need to implant additional microparticles. However, in some instances, it may be desirable or necessary to implant additional microparticles 100, such as, but not limited to, when a desired therapeutic effect or temperature was not achieved. In some instances, a hyperthermic treatment may be performed daily, a few times a week, weekly, bi-weekly, monthly, etc., as desired to achieve the desired treatment. In some instances, the therapeutic device 100 may be configured to remain in the body for a period of three to six months. The device 100 may slowly degrade over this time but remain large enough to perform the desired hyperthermic treatment. As the device 100 degrades, the device 100 may produce by-products that are not harmful to the surrounding tissue and are easily resorbed or expelled from the body.

In some instances, it may be desirable to deliver a therapeutic drug in combination with a hyperthermic treatment. In some instances, the device 100 may include a therapeutic drug 106 incorporated into the microparticle 100 (intermixed with the first material 104 and the second material 106) or a coated onto an outer surface of the body of the device 100. The heat generated by the Curie temperature material 104 may trigger a release of a therapeutic drug and/or heat the surrounding tissue to provide hyperthermic treatment. It is further contemplated that the implantable therapeutic device 100 could act as a temperature catalyst for another reaction in which a reaction or an activity is dormant until heat activated.

The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include chemotherapeutic agents, anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

The therapeutic drug may be a chemotherapeutic agent including, but not limited to, Everolimus, platins, such as carboplatin and cisplatin, taxanes such as docetaxel and paclitaxel; gemcitabine, VP16, mitomycin, idoxuridine, topoisomerase 1 inhibitors such as irinotecan, topotecan and camptothecins; nitrosoureas such as BCNU, ACNU or MCNU, methotrexate, bleomycin, adriamycin, cytoxan and vincristine; immunomodulating cytokines such as IL2, IL6, IL12 and IL13, and interferons. Certain chemotherapeutic agents are known to be potentiated by heating the tissue and/or the chemotherapeutic agent. Examples of possible heat-activated or heat-enhanced chemotherapeutic agents include bleomycin, BCNU, cisplatin, cyclophosphamide, melphalan, mitoxantrone, mitomycin C, thiotepa, misonidazole, 5-thi-D-glucose, amphotericin B, cysteine, cysteamine, and AET.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

Figure 2:
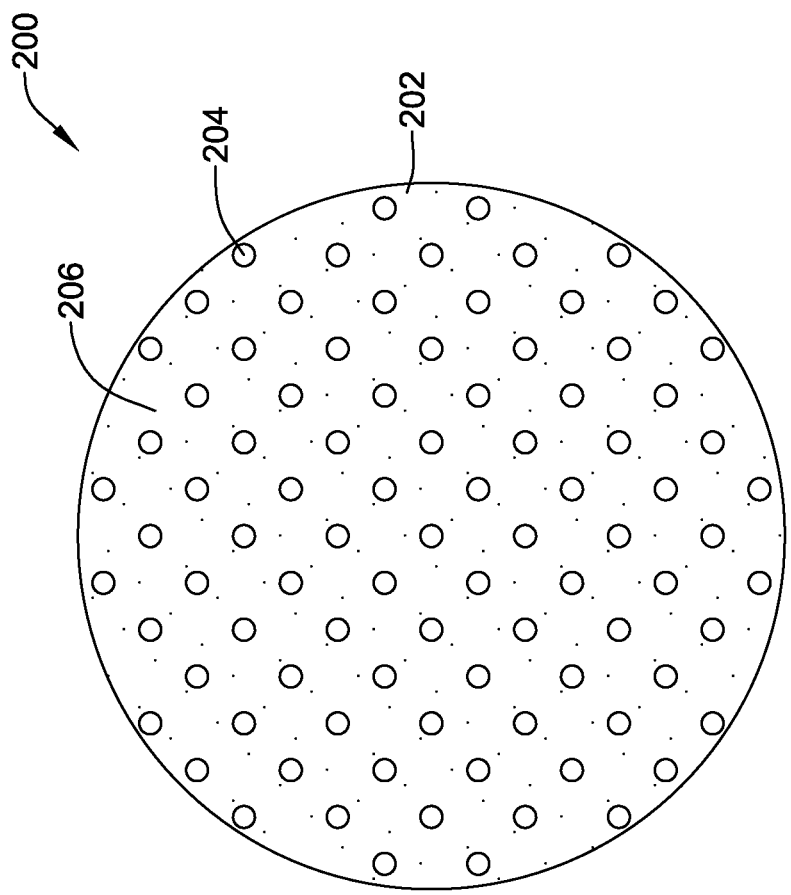
FIG. 2 is cross-sectional view of another illustrative microparticle.

FIG. 2 is a cross-sectional view of an embodiment of another illustrative implantable therapeutic device 200. In some embodiments, the implantable therapeutic device 200 comprises a microparticle or a nanoparticle. The therapeutic device 200 may have a generally spherical shape, although this is not required. For example, the therapeutic device 200 may be rod-shaped, elliptical, or an eccentric shape. It is contemplated that the therapeutic device 200 may take any shape desired. As discussed above, as individual particle sizes of Curie temperature materials increase, they more closely represent properties of the bulk material including magnetic susceptibility and Curie temperature. The use of nanoparticles of iron, iron oxide, iron alloy, and iron oxide alloy particles may allow the Curie temperature and magnetic moment coupling of a plurality of grouped nanoparticles into a compound (e.g. forming a larger particle made up of a plurality of smaller particles) to behave more like a smaller, non-bulk compound or particle. This compound may have more controllable Curie temperatures. Such nanoparticles may be compounded into a polymer or joined with another material to achieve the desired particle size, while avoiding variable Curie points within the overall particle (avoiding hot spots). For example, the nanoparticles may be homogenously, or uniformly, distributed throughout the polymer. However, in some instances it may be desirable to distribute the nanoparticles in a non-homogenous manner. When exposed to a magnetic field, such as a radiofrequency magnetic field, it is contemplated that the temperature of the compounded nanoparticles will be uniform and/or lacking hot spots.

In some embodiments, the implantable therapeutic device 200 includes a first compounding material 202 and a plurality of nanoparticles 204. The plurality of nanoparticles 204 may be homogenously or heterogeneously distributed through the first material 202, as desired. While the plurality of nanoparticles 204 are referred to as "nano" particles, it is contemplated that the particles 204 may have a particle size smaller than one nanometer. For example, the nanoparticles 204 may have a particle size in the range of 0.1 nanometers (or 1 angstrom) to 1,000 nanometers. In some instances, the nanoparticles 204 may have a particle size in the range of 30 to 50 nm. The compounding material 202 may comprise a variety of biocompatible thermoplastic polymers or ceramics, or any combination thereof. The compounding material 202 may be selected such that it does not reflow due to heat therapy and degrades over time. Examples of these biocompatible thermoplastic polymers include, but are not limited to, polyglycolide (PGA), copolymers of glycolide such as glycolide/L-lactide copolymers (PGA/PLLA), glycolide/trimethylene carbonate copolymers (PGA/TMC); polylactides (PLA), stereocopolymers of PLA such as poly-L-lactide (PLLA), Poly-DL-lactide (PDLLA), L-lactide/DL-lactide copolymers; copolymers of PLA such as lactide/tetramethylglycolide copolymers, lactide/trimethylene carbonate copolymers, lactide/δ-valerolactone copolymers, lactide ε-caprolactone copolymers, polydepsipeptides, PLA/polyethylene oxide copolymers, unsymmetrically 3,6-substituted poly-1,4-dioxane-2,5-diones; poly-β-hydroxybutyrate (PHBA), PHBA/β-hydroxyvalerate copolymers (PHBA/HVA), poly-β-hydroxypropionate (PHPA), poly-p-dioxanone (PDS), poly-δ-valerolatone, poly-ε-caprolactone, methylmethacrylate-N-vinyl pyrrolidone copolymers, poly-esteramides, polyesters of oxalic acid, polydihydropyrans, polyalkyl-2-cyanoacrylates, polyurethanes (PU), polyvinyl alcohol (PVA), polypeptides, poly-β-maleic acid (PMLA), poly-β-alkanoic acids, or any combination thereof. Examples of biocompatible ceramics include, but are not limited to, calcium phosphate-based ceramics such as hydroxyapatite (HAP), tricalcium phosphate β (β TCP), and a mixture of HAP and β TCP.

The plurality of nanoparticles 204 may comprise a Curie temperature material and, in some instances, may be magnetic nanoparticles that are made of Curie materials. The term "magnetic nanoparticles" includes anti-ferromagnetic, ferromagnetic, and ferrimagnetic materials. In some embodiments, the first material 202 and/or the plurality of nanoparticles 204 is formed from one or more materials such that plurality of nanoparticles 204 have a selected Curie temperature ($T_c$) between 35° C. and 100° C. In other embodiments, the plurality of nanoparticles may have a Tc in the range of 40° C. to 45° C. or 50° C. to 70° C. In some embodiments, the plurality of nanoparticles 204 have a Curie temperature of approximately 80° C. or 90° C. When the plurality of nanoparticles 204 are subjected to an alternating magnetic field, the plurality of nanoparticles 204 undergo power dissipation in the form of heat caused by relaxation phenomena of the particles' magnetic moments following the electromagnetic field and the mechanical rotation of particles themselves within the dispersant medium. At temperatures less than the Curie temperature ($T<T_c$), the plurality of nanoparticles 204 are ferro- (or ferri-) magnetic, whereas the second material 104 transitions into a paramagnetic phase to stabilize the plurality of nanoparticles' 204 temperature at the predetermined Curie temperature. In some embodiments, the plurality of nanoparticles 204 includes one or more of gallium, iron, iron oxides, iron alloys, and/or iron oxide alloys cobalt, or nickel, or compounds thereof. In one or more embodiments, the Curie temperature material includes one or more of gallium arsenide, dysprosium, cobalt, magnetite, and neodymium. Numerous additional Curie temperature materials useful for the practice of the present invention may be selected from those described in commonly assigned U.S. patent application Ser. No. 14/689,605, the entire disclosure of which is hereby incorporated by reference.

The plurality of nanoparticles 204 may be compounded into the first material 202 to form a therapeutic device 200 having a desired size. For example, the therapeutic device 200 may range in size from approximately 1 nm to 1,000 nm or 1 μm to 3,000 μm, based on the intended purpose for treatment of the tissue. The implantable therapeutic device 200 can also be smaller than 1 micron and larger than 30 microns, as desired. For example, the implantable therapeutic device 200 may be sized according the location in which it is to be implanted.

In some embodiments, the percentage of the plurality of nanoparticles 204 in the therapeutic device 200 (e.g., by weight percent) may depend on a variety of factors, for example: (1) the type of treatment, (2) the amount of heat required for treatment, (3) the type of body tissue, etc. In some embodiments, the plurality of nanoparticles 204 comprise at least 2% of the device 200 by weight. In some embodiments, however, the plurality of nanoparticles 204 comprise at least 3% of the device 200 by weight. Other suitable percentages of the plurality of nanoparticles 204 in the device 200 may include at least 4%, 5%, 8%, 15%, etc., by weight. It should be noted that any other suitable percentage of the plurality of nanoparticles 204 may also be contemplated, without departing from the scope of the present disclosure.

It is contemplated that the percentage of the plurality of nanoparticles 204, the types of materials 202, 204, and/or size of the particles 204 used to may be selected to achieve an appropriate Curie temperature, a desired magnetic susceptibility, biocompatibility, location stability, and/or particle elimination (post therapy).

Once implanted, the therapeutic device 200 may be subjected to an alternating electric or magnetic field. It is contemplated that the therapeutic device 100 can be injected directly into tissue or delivered to a desired treatment region via the arterial system. The electric or magnetic field may be applied from a location external to the body and directed at the location of the therapeutic device(s) 200. When subjected to a field of sufficient intensity, the therapeutic device 200 heats up to a characteristic temperature at which the magnetic properties of the plurality of nanoparticles 204 switch to paramagnetic properties and at which the temperature of the Curie temperature material stops increasing. The device 200 heats only in the presence of a specified electric or magnetic field and frequency and only to the Curie temperature of the nanoparticles 204. When the Curie temperature is reached, the material goes from magnetic to non-magnetic, discontinuing the heating. This is a cyclic process that permanently and rapidly maintains the therapeutic device 200 temperature at the set Curie point of the material, as long as the electric or magnetic field is applied.

It is contemplated that the therapeutic device 200 may be configured to remain in the body for a desired period of time. For example, the therapeutic device 200 may be used to deliver hyperthermic treatments in combination with chemotherapy or radiation in the treatment of cancer. These treatments may be delivered over a period of weeks or months. In some instances, the therapeutic device 200 may be configured to remain in the body for a period of three to six months. The device 200 may slowly degrade over this time but remain large enough to perform the desired hyperthermic treatment. As the device 200 degrades, the device 200 may produce by-products that are not harmful to the surrounding tissue and are easily resorbed or expelled from the body.

In some instances, it may be desirable to deliver a therapeutic drug in combination with a hyperthermic treatment. In some instances, the device 200 may include a therapeutic drug 206 incorporated into the microparticle or a coated onto an outer surface of the device 200. The heat generated by the plurality of nanoparticles 204 may trigger a release of a therapeutic drug and/or heat the surrounding tissue to provide hyperthermic treatment. It is further contemplated that the implantable therapeutic device 200 could act as a temperature catalyst for another reaction in which a reaction or an activity is dormant until heat activated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable microparticle comprising:
    a generally spherical body comprising:
        a first material comprising a biodegradable magnesium based compound or a biodegradable magnesium based alloy; and
        a second material, different than the first material, comprising one or more of gallium arsenide, dysprosium, lanthanum iron oxide, lanthanide particles, LaFe—Si—H particles, cobalt, and neodymium, wherein the second material is distributed throughout the first material to avoid hot spots within the microparticle;
    wherein the first material is a non-Curie temperature material or has a Curie temperature lower than a Curie temperature of the second material; and
    wherein the first material and the second material form a composite having a Curie temperature in a range of 35° C. and 100° C.

2. The implantable microparticle of claim 1, wherein a ratio of the first material to the second material is greater than 1:1.

3. The implantable microparticle of claim 1, wherein the first material comprising the biodegradable magnesium based compound or the biodegradable magnesium based alloy is configured to degrade via oxidative corrosion.

4. The implantable microparticle of claim 1, wherein the first material further comprises a biocompatible polymer.

5. The implantable microparticle of claim 1, wherein the second material comprises a plurality of nanoparticles.

6. The implantable microparticle of claim 5, wherein the plurality of nanoparticles each have a particle size in the range of 0.1 to 2.5 nanometers.

7. The implantable microparticle of claim 1, further comprising a therapeutic agent.

8. The implantable microparticle of claim 7, wherein the therapeutic agent is disposed on an outer surface of the spherical body.

9. The implantable microparticle of claim 7, wherein the therapeutic agent is intermixed with the first material and the second material.

10. The implantable microparticle of claim 1, wherein the microparticle is configured to degrade over a period of time in the range of 3 to 6 months.

11. The implantable microparticle of claim 1, wherein the microparticle has a diameter in the range of 1-3000 microns.

12. The implantable microparticle of claim 1, the generally spherical body further comprising a third Curie temperature material.

13. An implantable microparticle comprising:
    a first material comprising a biodegradable magnesium based compound or a biodegradable magnesium based alloy; and
    a second material, different than the first material, comprising an iron oxide, wherein the second material is distributed throughout the first material to avoid hot spots within the microparticle;
    wherein the first material and the second material form a composite having a ratio of greater than 1:1 and a Curie temperature in the range of 35° C. and 100° C.

14. The implantable microparticle of claim 13, wherein the iron oxide comprises at least one of iron (III) oxide ($Fe_2O_3$), iron (II, III) oxide ($FeO.Fe_2O_3$), or magnesium oxide iron (III) oxide ($MgO.Fe_2O_3$).

15. A method of delivering therapeutic heat to a location within a body, the method comprising:
    implanting at least one microparticle into the body adjacent to a desired treatment region, the microparticle comprising:
    a generally spherical body having a diameter in the range of 1-3000 microns comprising:
        a first material comprising a biodegradable magnesium based compound or a biodegradable magnesium based alloy; and
        a second material, different than the first material, the second material comprising a plurality of iron oxide nanoparticles, wherein the second material is distributed throughout the first material to avoid hot spots within the microparticle;
    wherein the first material is a non-Curie temperature material or has a Curie temperature lower than a Curie temperature of the second material; and
    wherein the first material and the second material form a composite having a Curie temperature in the range of 35° C. and 100° C.;
    generating a magnetic field at a location adjacent to the microparticle for a period of time to heat the microparticle to its Curie temperature; and
    maintaining the microparticle at its Curie temperature for a period of time to achieve the desired therapeutic effect.

16. The method of claim 15, wherein the steps of generating a magnetic field and maintaining the microparticle at its Curie temperature are repeated in discrete sessions separated by a length of time.

17. The method of claim 16, wherein the steps of generating a magnetic field and maintaining the microparticle at its Curie temperature are repeated without implanting any additional microparticles.

18. The method of claim 15, wherein the microparticle further comprise a therapeutic agent.

* * * * *